United States Patent [19]

Andou et al.

[11] Patent Number: 5,252,469
[45] Date of Patent: Oct. 12, 1993

[54] PROCESS FOR PRODUCING A TRANSGLUTAMINASE DERIVED FROM STREPTOMYCES

[75] Inventors: Hiroyasu Andou; Akira Matsuura; Susumu Hirose, all of Aichi, Japan

[73] Assignee: Amano Pharmaceutical Co., Ltd., Aichi, Japan

[21] Appl. No.: 750,160

[22] Filed: Aug. 26, 1991

[30] Foreign Application Priority Data

Aug. 27, 1990 [JP] Japan .................................. 2-226076

[51] Int. Cl.$^5$ .................. C12P 21/04; C12N 9/10; C12N 9/78
[52] U.S. Cl. ................................... 435/71.2; 435/193; 435/227; 435/71.1
[58] Field of Search .................. 435/227, 193, 71.2

[56] References Cited

U.S. PATENT DOCUMENTS 5,055,310 10/1991 Nonaka et al. ................... 426/46
5,156,956 10/1992 Motoki et al. .................... 435/68.1

FOREIGN PATENT DOCUMENTS 0379606 8/1990 European Pat. Off. .

OTHER PUBLICATIONS

Goodfellow et al. (1984) "The Biology of the Actinomycetes", pp. 16–17, Acad. Press, N.Y.
ATCC Catalog of Bacteria & Bacteriophages (1989) 17th Ed., pp. 229, 246–247.

*Primary Examiner*—Douglas W. Robinson
*Assistant Examiner*—Jon P. Weber
*Attorney, Agent, or Firm*—Sughrue, Mion, Zinn, Macpeak & Seas

[57] ABSTRACT

A process for producing a transglutaminase which comprises (1) culturing a microorganism having the identifying characteristics of a microorganism selected from the group consisting of Streptomyces sp. No. 83, deposited as FERM BP-3505, Streptomyces lavendulae No. 466, deposited as FERM BP-3506, and mutants thereof, wherein the microorganism is capable of producing a transglutaminase, wherein the transglutaminase is an enzyme which catalyzes an acyl transfer reaction of a γ-carboxyamide group of a glutamine residue in a peptide or protein chain in the presence or absence of $Ca^{++}$ and wherein the transglutaminase has an isoelectric point of 10 or 6.8, respectively, and is inhibited by Pb ions, and (2) recovering the transglutaminase from the culture obtained is disclosed.

4 Claims, 4 Drawing Sheets

PROCESS FOR PRODUCING A TRANSGLUTAMINASE DERIVED FROM STREPTOMYCES

FIELD OF THE INVENTION

The present invention relates to a process for producing a transglutaminase derived from the genus Streptomyces, and more precisely, to a process for producing a transglutaminase which comprises culturing a microorganism belonging to the genus Streptomyces, which is capable of producing a transglutaminase and harvesting the transglutaminase from the culture obtained.

BACKGROUND OF THE INVENTION

Transglutaminases are enzymes which catalyze an acyl transfer reaction of a γ-carboxyamide group of a glutamine residue in a peptide or protein chain.

The transglutaminases form intramolecular or intermolecular ε-(γ-Glu)-Lys cross-linking wherein the ε-amino group of the lysine residue in the protein serves as the acyl receptor. When water functions as the acyl receptor, the transglutaminases catalyze deamination of glutamine residues to form glutamic acid residues.

The protein gelation products obtained utilizing the transglutaminases according to the present invention are used as yoghurt, jelly, cheese, gel cosmetics, etc., including conventional gel foodstuffs and gel cosmetics.

In the animal-derived transglutaminase, there are hitherto known, the transglutaminases which are widely distributed in, for example, liver of the guinea pig (Connellan, et al., Journal of Biological Chemistry, Vol. 246, No. 4, pages 1093-1098 (1971)) and mammal organs and blood (Folk et al., Advances in Enzymology, Vol. 38, pages 109-191 (1973) and Folk et al., Advances in Protein Chemistry, Vol. 31, page 1-133 (1977)) and characteristics of the enzymes have been investigated.

However, application of the animal-derived transglutaminase to industry, particularly, the process for producing protein gelation products involves defects as described below.

It is difficult to obtain animal-derived transglutaminases at low cost and in large quantities. Also, there is the restriction that at least 1 unit of this expensive enzyme and at least 2.0 wt. % of a substrate protein concentration per 1 g of substrate protein are required for gelation. Further, the animal-derived transglutaminase is calcium ($Ca^{2+}$)-dependent so that its application is limited.

Because of the foregoing defects, processes for producing gelation products using animal-derived transglutaminases are impractical.

Also, in view of the above difficulties of applying animal-derived transglutaminases in an industrial setting, a microorganism-derived transglutaminase which is produced by the genus Streptoverticillium has previously been proposed by the present inventors in European Patent Publication No. 0 379 606A1.

SUMMARY OF THE INVENTION

As a result of farther extensive investigation which has been made in search of a broad spectrum of microorganisms for use in the production of a transglutaminase, it has been found that the microogranisms belonging to the genus Streptomyces are capable of producing transglutaminases which catalyze an acyl transfer reaction of the γ-carboxyamide group of a glutamine residue in a peptide or protein chain in the presence and absence of $Ca^{2+}$. The present invention is based on these findings.

It is therefore one object of the present invention to provide a process for producing a transglutaminase which is free from problems such as quantity of supply, cost/performance, and ease of purification.

It is another object of the present invention to provide a process for producing a transglutaminase which has great practicality since no calcium is required for the reaction catalyzed by the transglutaminase.

The above and other objects, which will become more readily apparent hereinafter, have been achieved by a process for producing a transglutaminase which comprises culturing a microorganism belonging to the genus Streptomyces, which is capable of producing a transglutaminase and harvesting the transglutaminase from the culture obtained.

BRIEF DESCRIPTION OF THE DRAWINGS

A more complete appreciation of the invention and many of the attendant advantages thereof will be readily obtained as the invention becomes better understood by reference to the following detailed description when considered in connection with the accompanying drawing, wherein.

DETAILED DESCRIPTION OF THE INVENTION

Figure 1:
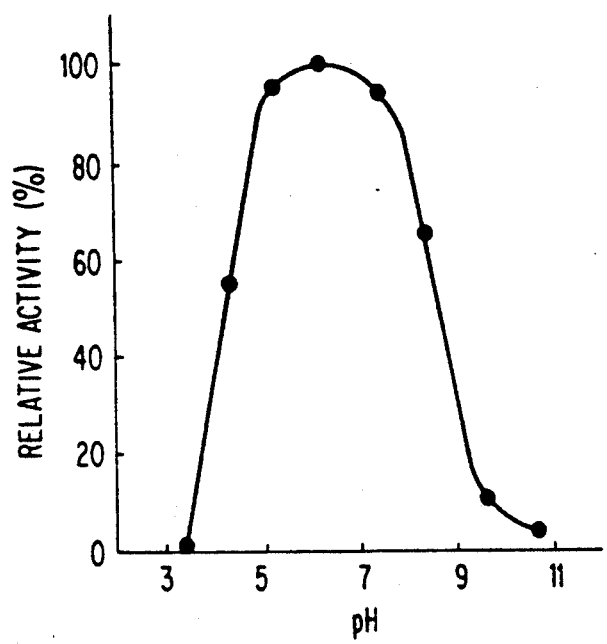
FIGS. 1, 2, 3 and 4 show an optimum pH curve, optimum temperature curve, pH stability curve and temperature stability curve of Enzyme No. 83 of the present invention, respectively.

As specific examples of the microorganisms belonging to the genus Streptomyces which can be used in the present invention, the following Streptomyces sp. No. 83 (hereafter, referred to as Strain No. 83) and *Streptomyces lavendulae* No. 466 (hereafter, referred to as Strain No. 466) which the present inventors isolated from soil samples may be mentioned.

The bacteriological characteristics of these new strains are set forth below. The experimental procedures used for taxonomical identification were those described in Experimental Methods for Identification of Actinomycetes, Japan Society for Actinomyces Research (1985), Classification and Identification of Microorganisms, Gakkai Shuppan Center (1975), and Experimental Methods for Chemical Classification of Microorganisms, Gakkai Shuppan Center (1982).

As references for classification and identification, Bergey's Manual of Determinative Bacteriology 8th Ed. (1974), Determinative Bacteriology 7th Ed. and 8th Ed., International Journal of Systematic Bacteriology 19, (1969) and 28 (1978), and Experimental Methods for Identification of Actinomycetes (1985) were used. As to colors, JIS Standard Color Cards, Japan Standards Association (1972), were referred to.

Bacteriological characteristics of Strain No. 83 and Strain No. 466 a. Morphologic characteristics The morphologic characteristics are shown in Table 1.

TABLE 1

| Morphologic Characteristics | Strain No. 83 | Strain No. 466 |
|---|---|---|
| Sporulated mycelium | | |
| Mode of branching | monopodial | monopodial |
| Spore morphology | straight (R), open loops (RA) | flexuous (F), straight (R) |
| Spores | | |
| Number | ≧50 | 5–10 |
| Spore wall ornamentation | smooth | smooth |
| Shape | oblong~oval | oblong~oval |
| Size, μ | 0.8 × 0.8 – 1.6 | 0.6 – 1.0 × 1.0 – 1.6 |
| Motility | none | none |
| Sporangium | none | none |
| Vegetative mycelium | | |
| Fragmentation | not fragmented | not fragmented |
| Sclerotium | | |
| Formation | none (ball-like mass) | none |
| Sporangiophore | | |

TABLE 1-continued

| Morphologic Characteristics | Strain No. 83 | Strain No. 466 |
|---|---|---|
| Position | on aerial and vegetative mycelia | on vegetative mycelia |
| Vegetative mycelium | | |
| Growth | zigzag | zigzag |
| Aerial mycelium | | |
| Growth | good | poor |
| Mode of branching | radial | radial |
| Sporangiophore | | |
| Length | short | short |
| Branching | dichotomous | | b. Cultural characteristics in terms of growth and color

The cultural characteristics in terms of growth and color of Strain No. 83 and Strain No. 466 on various media (incubated at 28° C. and observed for 30 days) are set forth in Tables 2 and 3, respectively.

TABLE 2

(Cultural Characteristics of Strain No. 83)

| Medium | Vegetative Mycelium, Growth and Color | Aerial Mycelium, Growth and Color | Reverse Color of Vegetative Mycelium | Diffusible Pigment |
|---|---|---|---|---|
| Sucrose nitrate agar | (+) colorless | (+) reddish brown | Ivory | none |
| Glycerin asparagine agar (ISP No. 5) | (++) colorless | (++) white | light yellow | none |
| Starch inorganic salt agar (ISP No. 4) | (++) | (+++) reddish brown (5YR 2/8) | yellow (5Y 9/4) | none |
| Tyrosine agar (modified Okanishi medium) | (++) | (++) white | reddish brown (2.5YR 6/3) | none |
| Yeast molt agar (ISP No. 2) | (+++) colorless | (+++) Reddish brown (5R 6/3) | yellow (2.5Y 8/6) | none |
| Bennet's agar | (++) | (+) white~reddish brown (5R 8/3) | yellow (5Y 8/4) | none |
| Peptone yeast iron agar (ISP No. 6) | (++) brown (2.5Y 4/4) | (±) | yellowish brown (10YR 6/4) | none |
| Peptone yeast starch agar | (+++) colorless | (+++) reddish brown (5R 6/3) | yellow (2.5Y 8/6) | none |

±: Sparse
+ ~ +++: Poor to luxuriant

TABLE 3

(Cultural Characteristics of Strain No. 466)

| Medium | Vegetative Mycelium, Growth and Color | Aerial Mycelium, Growth and Color | Reverse Color of Vegetative Mycelium | Diffusible Pigment |
|---|---|---|---|---|
| Sucrose nitrate agar | (+) colorless | white | colorless | none |
| Glycerin asparagine agar (ISP No. 5) | (++) scarlet (2.5R 6/8) | (+) pinkish white | scarlet (2.5R 6/8) | light yellowish brown |
| Starch inorganic salt agar (ISP No. 4) | (++) scarlet (center | (+) pinkish white | yellowish brown (5Y 8/2) | none |
| Tyrosine agar (modified Okanish medium | (++) | (+) brown | brown (2.5YR 3/2) | brown |
| Nutrient agar | (+) light brown | (−) | brown (2.5YR 4/4) | brown |
| Yeast molt agar (ISP No. 2) | (++) colorless | (±) | (7.5Y 6/5) | light yellowish brown |
| Bennet's agar | (++) scarlet | (±) | | none |
| Peptone yeast iron agar (ISP No. 6) | (++) yellowish brown (10Y 7/4) | (−) colorless | yellowish brown (10Y 7/4) | none |
| Peptone yeast starch agar | (++) colorless~ | (+) pinkish | scarlet (7.5Y 5/10) | light yellowish |

TABLE 3-continued (Cultural Characteristics of Strain No. 466)

| Medium | Vegetative Mycelium, Growth and Color | Aerial Mycelium, Growth and Color | Reverse Color of Vegetative Mycelium | Diffusible Pigment |
| --- | --- | --- | --- | --- |
| | scarlet | white | | brown |

±: Sparse
+ ~ + + +: Poor to luxuriant c. Physiologic characteristics

The temperature range for growth and other characteristics such as gelatin liquefaction, starch hydrolysis, skin milk coagulation/peptonization, melanoid pigment production and hydrogen sulfide production of the respective strains are shown in Table 4. The carbon source assimilation spectrum (Pridham & Gottlieb basal agar) of each strain is shown in Table 5.

d. Chemical characteristics

The results of analysis for cell wall amino acid composition and intracellular diaminopimelic acid are shown in Table 4.

TABLE 4

| | Strain No. 83 | Strain No. 466 |
| --- | --- | --- |
| Temperature range for growth (°C.) | 15–37 | 15–39 |
| Optimal temperature for growth (°C.) | 30–34 | 32–37 |
| Hydrolysis of starch | + | + |
| Coagulation of skim milk | − | − |
| Peptonization of skim milk | − | + |
| Production of melanoid pigment (Okanishi method) | − | + |
| Production of hydrogen sulfide | not produced | not produced |
| Liquefaction of gelatin | negative | negative |
| Reduction of nitrate (ISP No. 6) | positive | negative |
| NaCl tolerance (peptone yeast extract starch) | | |
| 4% | growth | growth |
| 7% | no growth | no growth |
| Catalase | produced | produced |
| Cell wall analysis | | |
| LL-diaminopimelic acid | present | present |
| meso-DAP | absent | absent |
| Total cell sugar | Rham, Gal, Rib | Rib |
| Cell well amino acids | Lys, Gly, Asp | Lys, Gly, Asp |
| Cell wall sugar | Rham, Gal | none |
| Gram's stain | + | + |
| Acid fastness | none | none |
| Dissolution of calcium malate | ++ | + |

Rham: rhamnose
Gal: galactose
Rib: Ribose
Lys: lysine
Gly: glycine
Asp: aspartic acid

TABLE 5

(Pridham & Gottlieb agar medium)

| | Strain No. 83 | Strain No. 466 |
| --- | --- | --- |
| Glucose | ++ | ++ |
| D-Xylose | − | − |
| L-Arabinose | − | − |
| L-Rhamnose | + | − |
| D-Fructose | +~ | − |
| D-Galactose | − | − |
| Raffinose | − | − |
| D-Mannitol | − | − |
| i-Inositol | − | − |
| Salicin | ++ | − |
| Sucrose | − | − |

TABLE 5-continued (Pridham & Gottlieb agar medium)

| | Strain No. 83 | Strain No. 466 |
| --- | --- | --- |
| Starch | +++ | +++ |

+++~+: Strongly utilized~utilized
±: doubtfully utilized
−: not utilized

Thus, these strains contain diaminopimelic acid in the cell wall and LL-diaminopimelic acid intracellularly but did not contain meso-diaminopimelic acid.

(1) Identification of Strain No. 83

Excepting the rare occurrence of open loops (RA), the spore chains are predominantly linear and markably elongated (arthrospore type chains of 50–80 spores), forming a ball-like mass depending on media. The strain produces abundant vegetative hyphae on yeast extract-containing media (e.g., ISP No. 2 medium), which are characterized by being velvety or downy and azuki-colored (reddish brown). The existence of LL-diaminopimelic acid and the absence of meso-diaminopimelic acid suggest that it belongs to cell wall type I. As to sugars, galactose and rhamnose were detected but neither arabinose nor xylose was found. These and other characteristics such as fragmentation of hyphae, spore chain morphology, spore motility, aerial mycelium, whorl formation, acid fastness and catalase production suggested that the strain belongs to the genus.

Streptomyces

Meanwhile, the carbon assimilation spectrum of the strain is relatively narrow, with starch, glucose, salicin, rhamnose and fructose (weak) only being assimilated. The above and other characteristics of the strain suggested that it is akin to Streptomyces cinnamonenois, Streptomyces nojiriensis and Streptomyces diastaticus. However, the strain differentiates itself clearly from the above-mentioned species in that it produces melanoid pigments and does not utilize rhamnose. Therefore, the strain was identified to belong to a new species of the genus Streptomyces and designated Streptomyces sp. No. 83.

(2) Identification of Strain No. 466

The aerial mycelium is usually so sparse that it looks like the vegetative mycelium exposed on the surface. Its color is scarlet. The colony surface is radial, filmy and hard, with hyphae characteristically extending well into the agar. As to spore chain morphology, comparatively short chains of arthrospores (5–10 spores) are produced on Pridham-Gottlieb starch medium but spore chains on most other media are not uniform, being spherical or hooked, with the hyphal end being indented in the form of a hump or branched. As to the cell wall composition, LL-diaminopimelic acid was detected but meso-diaminopimelic acid was absent, indicating that it corresponds to cell wall type I. The findings that the strain utilizes glucose and starch only and tolerates not more than 4% NaCl as well as its straight or digital spore morphology, red-series color of aerial mycelium and melanoid pigment production suggest that it is a strain of *Streptomyces xanthophaeus* or *Streptomyces flavotricini* according to Bergey's Manual, 8th Ed, or *Streptomyces lavendulae* according to the updated edition thereof, viz. Bergey's Manual of Systematic Bacteriology (1989). Therefore, the strain was identified to belong to the genus Streptomyces and designated *Streptomyces lavendulae* No. 466.

Incidentally, Streptomyces sp. No. 83 and *Streptomyces lavendulae* No. 466 have been deposited with the Fermentation Research Institute, Agency of Industrial Science and Technology 1-3, Higashi 1-chome, Tsukuba-shi, Ibaraki-ken 305, Japan on Aug. 13, 1990 under the respective deposit number of FERM No. P-11656 (FERM No. BP-3505 under Budapest Treaty) and FERM No. P-11657 (FERM No. BP-3506 under Budapest Treaty), respectively.

For the purposes of the present invention, any microorganism belonging to the genus Streptomyces, which is capable of producing transglutaminases can be successfully employed, preferably Streptomyces sp. No. 83 (Strain No. 83) and *Streptomyces lavendulae* No. 466 (Strain No. 466) described above.

Methods for culture, purification etc., which comprise culturing these microorganisms and harvesting transglutaminase (hereafter, referred to as BTGase) will be described below.

For the purposes of the present invention, any culturing mode of liquid culture and solid culture can be performed, but from an industrial standpoint, it is advantageous to perform deep aerial spinner culture. As culture sources to be used, there can be used carbon sources, nitrogen sources, inorganic salts and other trace nutrient sources conventionally used for culture of microorganisms; in addition thereto, all nutrient sources can be employed as long as they are utilizable by microoganisms belonging to the genus Streptomyces. As the carbon sources for media, there can be used, singly or in combination, glucose, sucrose, rastagen, glycerin, dextrin, starch, etc. and in addition thereto, fatty acids, oils and fats, organic acids, etc. As the nitrogen sources, any of inorganic nitrogen sources and organic nitrogen-sources can be used. As the inorganic nitrogen sources, there can be used ammonium nitrate, ammonium sulfate, sodium nitrate, ammonium chloride, etc.

Further as the organic nitrogen sources there can be used, for example, powder of soybean, rice, sweet corn and wheat etc., bran and defatted meal, and corn steep liquor, peptone, meat extract, casein, amino acids, yeast extract, etc. As the inorganic salts and the trace nutrient sources, there can be used salts of phosphoric acid, magnesium, potassium, iron, calcium, zinc, etc., and any other materials that can accelerate growth of the bacteria or production of BTGase such as vitamins, nonionic surfactants, defoaming agents, etc., if necessary. Culture may be performed under aerobic conditions at a culture temperature within such a range that the bacteria grow to product BTGase, preferably at 25° to 35° C. A time period for the culture varies depending upon conditions but the culture may be performed until BTGase is best produced, generally for about 2 to 4 days. In the case of liquid culture, BTGase is dissolved in the culture solution and can be harvested from the culture filtrate obtained by removing solid contents from the culture solution after completion of the culture.

For purification of BTGase from the culture filtrate, any method generally used for purification of enzymes can be used.

For example, there can be used treatment methods with an organic solvent such as ethanol, acetone, isopropyl alcohol, etc.; salting out using ammonium sulfate, sodium chloride, etc., dialysis, ultrafiltration, ion exchange chromatography, adsorption chromatography, gel filtration, adsorbents, isoelectric point fractionation, etc. Further, in the case where the purity of BTGase is increased by the use of these methods in suitable combination, the methods can be performed in such a combination. From the enzyme obtained by these methods, liquid or solid BTGase can be obtained by methods of ultrafiltration condensation, reverse osmosis condensation, drying under reduced pressure, freeze drying or spray drying, by adding a variety of salts, sugars, proteins, lipids, surfactants, etc., as stabilizers or without adding them.

Measurement of the activity of BTGase is carried out by performing a reaction using benzyloxycarbonyl-L-glutaminyl glycine and hydroxylamine as substrates in the absence of $Ca^{2+}$, forming an iron complex with the resulting hydroxamic acid in the presence of trichloroacetic acid, measuring absorption at 525 nm and determining the amount of hydroxamic acid by a calibration curve to calculate the activity. The BTGase activity is measured by the method described below, unless otherwise indicated.

Measurement of Activity

Reagent A
0.2 M Tris-hydrochloride buffer (pH 6.0)
0.1 M hydroxylamine
0.01 M reductive glutathione
0.03 benzyloxycarbonyl-L-glutaminyl glycine Reagent B
Reagent B is made of equal volumes of the following component.
3 N hydrochloric acid
12% trichloroacetic acid
5% $FeCl_3.6H_2O$ (dissolved in 0.1 N-HCl)

To 0.05 ml of an enzyme solution is added 0.5 ml of Reagent A and they are mixed with each other. After reacting at 37° C. for 10 minutes, Reagent B is added thereto to discontinue the reaction and form an Fe complex. Thereafter, absorbance is measured at 525 nm. As a control, absorbance is measured after reacting a previously thermally inactivated enzyme solution in a similar manner and a difference in absorbance between the control and the enzyme solution is measured. Separately, a calibration curve is prepared using L-glutamic acid γ-monohydroxamic acid instead of the enzyme solution, and the amount of hydroxamic acid produced is determined by the difference in absorbance described above. An enzyme activity which produces 1 μmol of hydroxamic acid per 1 minute is defined as 1 unit.

Enzymological properties of the thus obtained purified BTGases, namely, transglutaminase of Streptomyces sp No. 83 (named Enzyme No. 83) and transglutaminase of *Streptomyces lavendulae* No. 466 (named Enzyme No. 466) are described below.

a) Optimum pH

Figure 5:
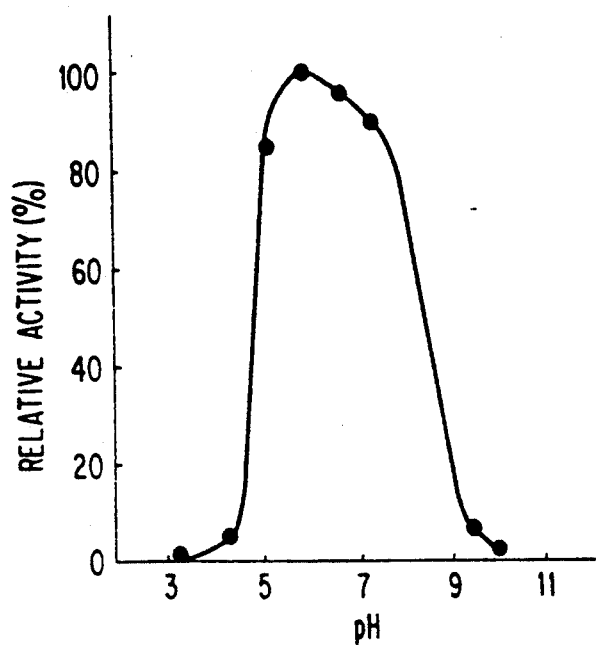
FIGS. 5, 6, 7 and 8 show an optimum pH curve, optimum temperature curve, pH stability curve and temperature stability curve of Enzyme No. 466 of the present invention, respectively.

In the case of using benzyloxycarbonyl-L-glutaminyl glycine, and hydroxylamine as substrate, each optimum pH of Enzyme No. 83 and Enzyme No. 466 lies in a range of approximately 6 to 7 upon the reaction at 37° C. for 10 minutes (shown in FIGS. 1 and 5).

b) Optimum temperature

Figure 2:
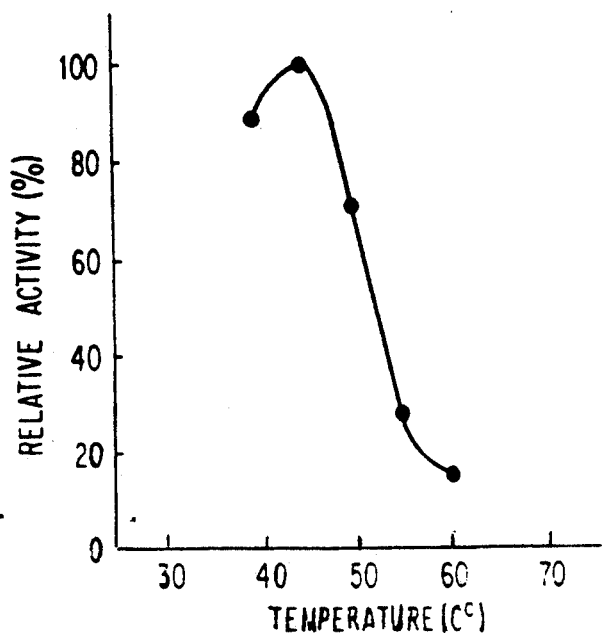
Figure 6:
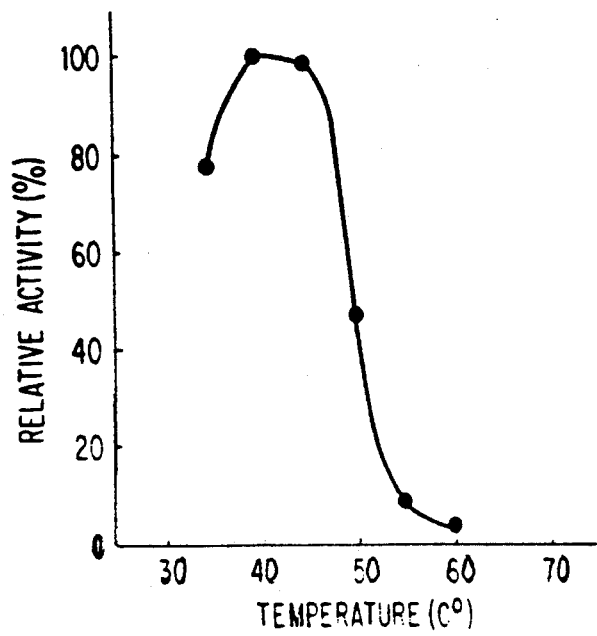

In the case of using benzyloxycarbonyl-L-glutaminyl glycine and hydroxylamine as substrates, each optimum temperature of Enzyme No. 83 and Enzyme No. 466 lies at about 40°~45° C. upon the reaction of pH 7 for 10 minutes (shown in FIGS. 2 and 6).

c) pH Stability

Figure 3:
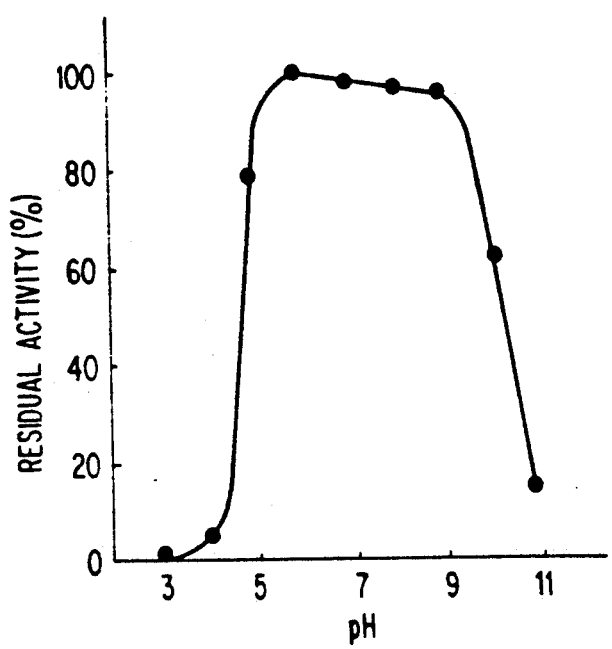
Figure 7:
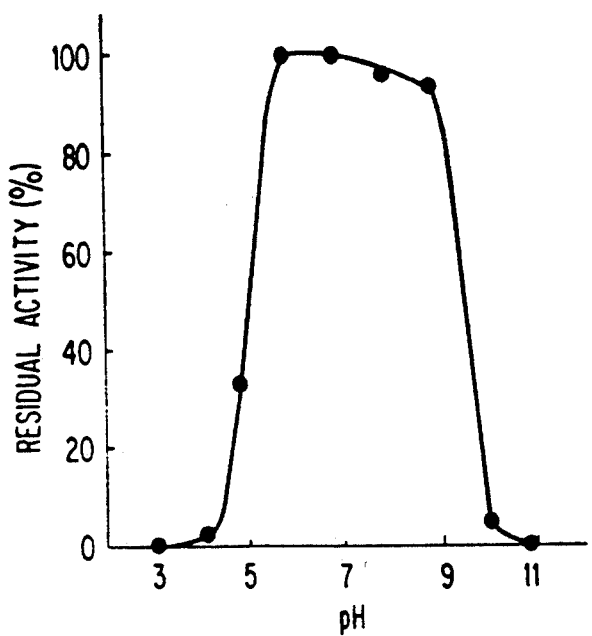

By treatment at 37° C. for 10 minutes, both Enzyme No. 83 and Enzyme No. 466 are stable at pH of 6 to 9 (shown in FIGS. 3 and 7).

d) Temperature stability

Figure 4:
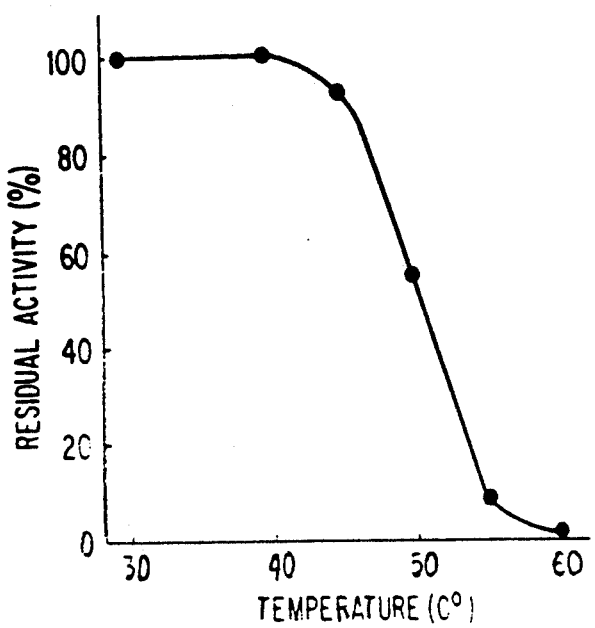
Figure 8:
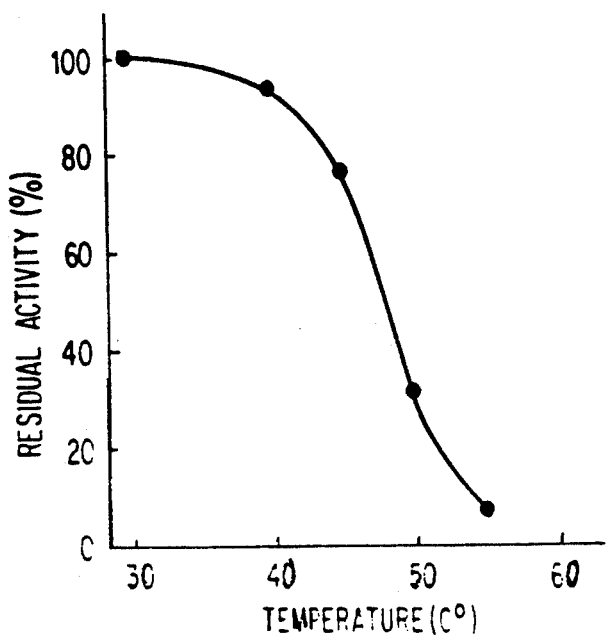

By treatment at pH 7 for 10 minutes, Enzyme No. 83 retains 100 activity at 40° C. and 55% at 50° C.; and Enzyme No. 466 retains 94% activity at 40° C. and 32% at 50° C. (shown in FIGS. 4 and 8).

e) Substrate specificity

Using each BTGase, reactions of various synthetic substrates with hydroxylamine were examined. No BTGase reacts with the synthetic substrates benzyloxycarbonylasparaginyl glycine, benzyloxycarbonyl glutamine and glycylglutaminyl glycine. However, the reactivity is the highest when the synthetic substrate is benzyloxycarbonylglutaminyl glycine. In this case, the concentration of various synthetic substrates is 5 mM. The results are shown in Table 6. In the table, CBZ, Gln, Gly and Asn are abbreviations for benzyloxycarbonyl group, glutaminyl group, glycyl group and asparaginyl group, respectively.

TABLE 6

| Substrate | Enzyme No. 83 | Enzyme No. 466 |
|---|---|---|
| CBZ—Gln—Gly | 100 | 100 |
| CBZ—Gln—Gly—OEt | 61 | 65 |
| CBZ—Gln—Gln—Gly | 49 | 35 |
| CBZ—Gly—Gln—Gly—Gly | 10 | 18 |
| CBZ—Gln | 0 | 0 |
| CBZ—Asn—Gly | 0 | 0 |
| Gly—Gln—Gly | 0 | 0 | f) Influence of metal ions

Various metal ions were added to the activity measurement system in a concentration of 1 mM (the results are shown in Table 7). In all BTGases, the activity is inhibited by $Cu^{2+}$, $Zn^{2+}$ and $Pb^{2+}$.

TABLE 7

| Metal Ion | Enzyme No. 83 (%) | Enzyme No. 466 (%) |
|---|---|---|
| None | 100 | 100 |
| $CaCl_2$ | 101 | 99 |
| $BaCl_2$ | 100 | 100 |
| $CoCl_2$ | 100 | 98 |
| $CuCl_2$ | 89 | 90 |
| $FeCl_3$ | 93 | 97 |
| KCl | 104 | 101 |
| $MgCl_2$ | 102 | 99 |
| $MnCl_2$ | 102 | 99 |
| NaCl | 102 | 98 |
| $NiCl_2$ | 101 | 99 |
| $PbCl_2$ | 59 | 32 |
| $SrCl_2$ | 100 | 97 |
| $ZnCl_2$ | 36 | 10 | g) Influence of inhibitor

Each inhibitor was added in a concentration of 1 mM. After allowing the mixture to stand at 25° C. for 30 minutes, the activity was measured (the results are shown in Table 8). In all BTGases, the activity is inhibited by p-chloromercury benzoic acid (simply referred to as PCMB), N-ethylmaleimide (simply referred to as NEM) and monoiodoacetic acid.

TABLE 8

| Inhibitor | Enzyme No. 83 | Enzyme No. 466 |
|---|---|---|
| None | 100 | 100 |
| EDTA | 103 | 108 |
| PCMB | 86 | 28 |
| NEM | 10 | 5 |
| Monoiodoacetic acid | 92 | 87 |
| PMSF | 101 | 103 |

In Table 8, PMSF is the abbreviation for phenylmethylsulfonyl fluoride.

h) Isoelectric point

According to ampholine isoelectric point electrophoresis, isoelectric points, pI of Enzyme No. 83 and pI of Enzyme No. 466 are at approximately 10 and 6.8, respectively.

i) Molecular weight

According to SDS disc electrophoresis, molecular weight of Enzyme No. 83 and Enzyme No. 466 are approximately 39,000.

Next, properties of BTGases are compared to those of guinea pig liver-derived transglutaminase. The guinea pig liver-derived transglutaminase was prepared by the method described in Connellan et al., Journal of Biological Chemistry, Vol. 246, No. 4, pp. 1093-1098 (1971). In Table 9, comparison in enzymological properties is shown and influence of $Ca^{2+}$ on activity is shown in Table 10. As will be apparent from Tables 9 and 10, various differences in enzymological properties are noted between transglutaminase of guinea pig liver (hereafter, referred to as MTGase) which has been mainly investigated heretofore and BTGases derived from the genus Streptomyces; in particular, differences are noted in temperature stability, molecular weight, isoelectric point and substrate specificity. Further, a difference is noted in that the BTGases of the present invention act in the presence and absence of $Ca^{2+}$. Therefore, the respective enzymes of the present invention are different from MTGase in their properties.

TABLE 9

| | Enzyme No. 83 | Enzyme No. 466 | MTGase |
|---|---|---|---|
| Optimum pH | ca. 6–7 | ca. 6–7 | 6 |
| pH Stability | 6–9 | 6–9 | 6–7.5 |
| Optimum temperature | ca. 40–45° C. | ca. 40–45° C. | 50–55° C. |
| Temperature stability (%) | | | |
| 40° C. residual rate | 100 | 94 | 96 |
| 50° C. residual rate | 55 | 32 | 40 |
| Molecular weight | ca. 39,000 | ca. 39,000 | ca. 90,000 |
| Isoelectric point | ca. 10 | ca. 6.8 | 4.5 |
| Substrate specificity (%) | | | |
| CBZ—Gln—Gly | 100 | 100 | 100 |
| CBZ—Gln—Gly—OEt | 61 | 65 | 122 |
| CBZ—Gln—Gln—Gly | 49 | 35 | 288 |
| CBZ—Gly—Gln—Gly—Gly | 10 | 18 | 126 |
| CBZ—Gln | 0 | 0 | 0 |
| CBZ—Asn—Gly | 0 | 0 | 0 |

TABLE 9-continued

| | Enzyme No. 83 | Enzyme No. 466 | MTGase |
|---|---|---|---|
| Gly—Gln—Gly | 0 | 0 | 0 |

TABLE 10

| Metal Ion | Enzyme No. 83 (%) | Enzyme No. 466 (%) | MTGase (%) |
|---|---|---|---|
| None | 99 | 99 | 0 |
| 1 mM CaCl$_2$ | 99 | 98 | 39 |
| 5 mM CaCl$_2$ | 100 | 100 | 100 |

The present invention is now illustrated in greater detail with reference to the following Examples, but it should be understood that the present invention is not deemed to be limited thereto.

EXAMPLE 1

Streptomyces sp No. 83 was inoculated on 200 ml of medium (pH 7) having a medium composition of 0.2% of polypeptone, 0.5% of glucose, 0.2% of dipotassium phosphate and 0.1% of magnesium sulfate followed by culturing at 30° C. for 48 hours. The obtained seed culture solution was added to 20 l of a medium (pH 7) containing 2.0% of polypeptone, 2.0% of rastagen (trademark, manufactured by Nichiden Kagaku K.K.), 0.2% of dipotassium phosphate, 0.1% of magnesium sulfate, 0.2% of yeast extract and 0.05% of Adekanol as a defoaming agent (trademark, manufactured by Asahi Denka Kogyo K.K.) followed by culturing at 30° C. for 3 days. After filtering, 18.5 l of the culture solution was obtained. The activity was 0.71 U/ml.

The culture solution was adjusted with hydrochloric acid to pH of 6.5 and passed through a column of CG-50 (trademark, manufactured by Organo Co., Ltd.), which had been previously equilibrated with 0.05 M phosphate buffer (pH 6.5). By this operation, transglutaminase was adsorbed. After washing protein impurities out with the same phosphate buffer solution, a density gradient of 0.05 to 0.5 M was prepared by the same buffer, through which the system was passed. The eluate was fractionated and recovered, and the fractions having a high specific activity were collected. After the system was diluted to have a conductivity of 10 ms or less, it was passed through a column of blue Sepharose. By this operation, transglutaminase was adsorbed. After washing protein impurities out with 0.05 M phosphate buffer (pH 7), a density gradient of 0 to 1 M was prepared by sodium chloride, through which the system was passed. The eluate was recovered and fractions having a high specific activity were collected. The fractions were desalted and rechromatographed on a column of CG-50 to fractionate the eluate. As a result, the active fraction eluted as a single peak. The specific activity was 356 times that of the culture filtrate and the recovery rate was 43%.

EXAMPLE 2

*Streptomyces lavendulae* No. 466 was inoculated into 200 ml of the same preculture medium as used in Example 1 and cultured at 30° C. for 48 hours. The resulting seed culture solution was added to 20 l of a medium (pH 7) containing 2.0% of polypeptone, 2.0% of glycerin, 0.2% of dipotassium phosphate, 0.1% of magnesium sulfate, 0.2% of yeast extract and 0.05% of Adekanol, which was then cultured at 30° C. for 3 days. The resulting culture broth was filtered to give 18.5 l of the culture filtrate. The activity of this culture solution was 2.47 U/ml.

Using a UF 6000 membrane, the culture solution was desalted and concentrated and the concentrate was adjusted to pH 7.0 with hydrochloric acid and passed through a column of DEAE-Cellulofine (trademark, manufactured by Seikagaku Kogyo), which had been previously equilibrated with 0.005 M phosphate buffer (pH 7.0). By this operation, transglutaminase was adsorbed on the column. The column was first washed with the same phosphate buffer solution to remove protein impurities and, then, elution was carried out with the same buffer on a density gradient of 0.005 to 0.5 M. The eluate was collected in fractions and the fractions having a high specific activity were collected. Then, using blue Sepharose and CG-50, the enzyme was purified as in Example 1 to give a pure enzyme giving a single peak in SDS disk electrophoresis. The specific activity relative to the culture filtrate was 169 times and the recovery rate was 37%.

As is apparent from above, the microorganism-derived BTGase of the present invention can be supplied at low cost and can be easily purified and therefore, is highly practical.

It is also advantageous that by the use of a BTGase according to the present invention, the research and development on various uses such as a food manufacturing or a medical treatment can be accelerated.

While the invention has been described in detail and with reference to specific embodiments thereof, it will be apparent to one skilled in the art that various changes and modifications can be made therein without departing from the spirit and scope thereof.

What is claimed is:

1. A process for producing a transglutaminase comprising the steps of:
    (1) culturing a microorganism having all of the identifying characteristics of the microorganism, Streptomyces sp. No. 83, deposited as FERM BP-3505, and mutants thereof, which produces a transglutaminase; and
    (2) recovering said transglutaminase from the culture obtained,
    wherein said transglutaminase is an enzyme which catalyzes an acyl transfer reaction of a γ-carboxyamide group of a glutamine residue in a peptide or protein chain in the presence or absence of Ca$^{++}$, and wherein said transglutaminase has an isoelectric point of 10, and is inhibited by Pb ions.

2. A process for producing a transglutaminase comprising the steps of:
    (1) culturing a microorganism having all of the identifying characteristics of the microorganism, *Streptomyces lavendulae* No. 466, deposited as FERM BP-3506, and mutants thereof, which produces a transglutaminase; and
    (2) recovering said transglutaminase from the culture obtained,
    wherein said transglutaminase is an enzyme which catalyzes an acyl transfer reaction of a γ- carboxyamide group of a glutamine rersidue in a peptide or protein chain in the presence or absence of Ca$^{++}$, and wherein said transglutaminase has an isoelectric point of 6.8, and is inhibited by Pb ions.

3. The process for producing a transglutaminase as claimed in claim 1, wherein said microorganism is Streptomyces sp. No. 83, deposited as FERM BP-3505.

4. The process for producing a transglutaminase as claimed in claim 1, wherein said microorganism is *Streptomyces lavendulae* No. 466, deposited as FERM BP-3506.

* * * * *